United States Patent
Mitsunaga et al.

(10) Patent No.: US 6,788,885 B2
(45) Date of Patent: Sep. 7, 2004

(54) SYSTEM FOR HEATING INSTILLATION OR TRANSFUSION LIQUIDS

(76) Inventors: Michael Mitsunaga, 21250 Hawthorne Blvd., Ste. 560, Torrance, CA (US) 90503; Yoshiaki Yamamoto, 21250 Hawthorne Blvd., Ste. 560, Torrance, CA (US) 90503

( * ) Notice: Subject to any disclaimer, the term of this patent is extended or adjusted under 35 U.S.C. 154(b) by 0 days.

(21) Appl. No.: 10/010,461

(22) Filed: Dec. 6, 2001

(65) Prior Publication Data

US 2002/0081109 A1 Jun. 27, 2002

Related U.S. Application Data (63) Continuation-in-part of application No. 09/653,692, filed on Sep. 1, 2000, now Pat. No. 6,336,003.

(51) Int. Cl.[7] .................................................. A61F 7/00
(52) U.S. Cl. ..................... 392/470; 392/484; 604/113
(58) Field of Search ................................ 392/470, 484; 604/93.01, 111, 113, 118, 151

(56) References Cited

U.S. PATENT DOCUMENTS

| | | | |
|---|---|---|---|
| 4,293,762 A | | 10/1981 | Ogawa |
| 4,574,876 A | * | 3/1986 | Aid .............................. 165/46 |
| 4,680,445 A | | 7/1987 | Ogawa |
| 4,735,609 A | | 4/1988 | Comeau et al. |
| 5,042,455 A | | 8/1991 | Yue et al. |
| 5,245,693 A | | 9/1993 | Ford et al. |
| 5,381,510 A | | 1/1995 | Ford et al. |
| 5,533,992 A | * | 7/1996 | Patel et al. ................. 604/403 |
| 6,146,359 A | | 11/2000 | Carr et al. |
| 6,175,688 B1 | * | 1/2001 | Cassidy et al. ............. 392/470 |
| 6,539,172 B2 | | 3/2003 | Akahane |
| 2001/0011585 A1 | | 8/2001 | Cassidy et al. |

* cited by examiner

*Primary Examiner*—Thor Campbell
(74) *Attorney, Agent, or Firm*—Philip K. Yu; East IP Group (57) ABSTRACT

A system for warming a fluid includes a fluid warmer having a housing that retains therein a heating element, and cartridge that is retained inside the housing and which receives heat from the heating element. The cartridge has a rigid plate having a first surface and a second opposing surface, with the plate having a meandering path provided therein. The cartridge also has a sheet of film that covers the first and second surfaces.

2 Claims, 6 Drawing Sheets

SYSTEM FOR HEATING INSTILLATION OR TRANSFUSION LIQUIDS

RELATED CASES

This is a continuation-in-part of application Ser. No. 09/653,692, filed Sep. 1, 2000, entitled "MAX ONE I.V. WARMER," now U.S. Pat. No. 6,336,003 B1, issued on Jan. 1, 2002, whose disclosure is incorporated by this reference as though set forth fully herein.

BACKGROUND OF THE INVENTION

1. Field of the Invention

The present invention relates to a system for heating or warming instillation or transfusion liquids.

2. Description of the Prior Art

Intravenous fluid (IV) is commonly used in hospitals, and is important for virtually all medical procedures and applications. Such IV fluid is typically delivered from an IV fluid bag into a blood vessel of a patient. In addition, where necessary, blood is also delivered from blood bags into a blood vessel of a patient. It is desirable to warm the blood or IV fluid to a certain range of temperatures (e.g., between 36.5 and 37 degrees Celsius) to prevent temperature drop in the patient which might lead to hypothermia.

According to a conventional technique for heating or warming an instillation liquid (such as IV fluid) or blood, and injecting the heated liquid, liquid drugs or blood (hereinafter collectively referred to as "fluid") into a blood vessel of a patient, a liquid feed pipe is passed through a warm water tank or a warming pad, or the fluid is passed through disposable bags or cartridges inside large cumbersome warming units to heat the fluid passing through the bags or cartridges up to an appropriate temperature.

These conventional techniques suffer from a number of drawbacks. For example, handling or transferring of the heating device can very troublesome. However, a greater concern is the consistency and quality of the warming. A number of the conventional fluid warming systems do not provide sufficiently good heat transfer to ensure that the fluid is being consistently warmed to the desired temperatures. For example, the liquid feed pipes, bags and cartridges used by these conventional systems are made of material(s), or are positioned in a manner, that do not promote effective heat transfer from the heating element inside the warming unit to the fluid through the feed pipes, bags and cartridges.

Thus, there remains a need to provide a heating device and cartridge that effectively and consistency warms fluid passing therethrough.

SUMMARY OF THE DISCLOSURE

It is an object of the present invention to provide a system that effectively warms fluid that is being passed therethrough.

It is another object of the present invention to provide a system that provides improved heat transfer from the heating elements in a heating device to fluid that is passed through a cartridge that is retained inside the heating device.

It is yet another object of the present invention to provide a disposable cartridge that can be used in a heating device, with the cartridge capable of facilitating effective and consistent heat transfer from the heating device to the fluid that is passed through the cartridge.

The objectives of the present invention are accomplished by providing a system for warming a fluid, the system including a fluid warmer having a housing that retains therein a heating element, and cartridge that is retained inside the housing and which receives heat from the heating element. The cartridge has a rigid plate having a first surface and a second opposing surface, with the plate having a meandering path provided therein. The cartridge also has a sheet of film that covers the first and second surfaces.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

Figure 1:
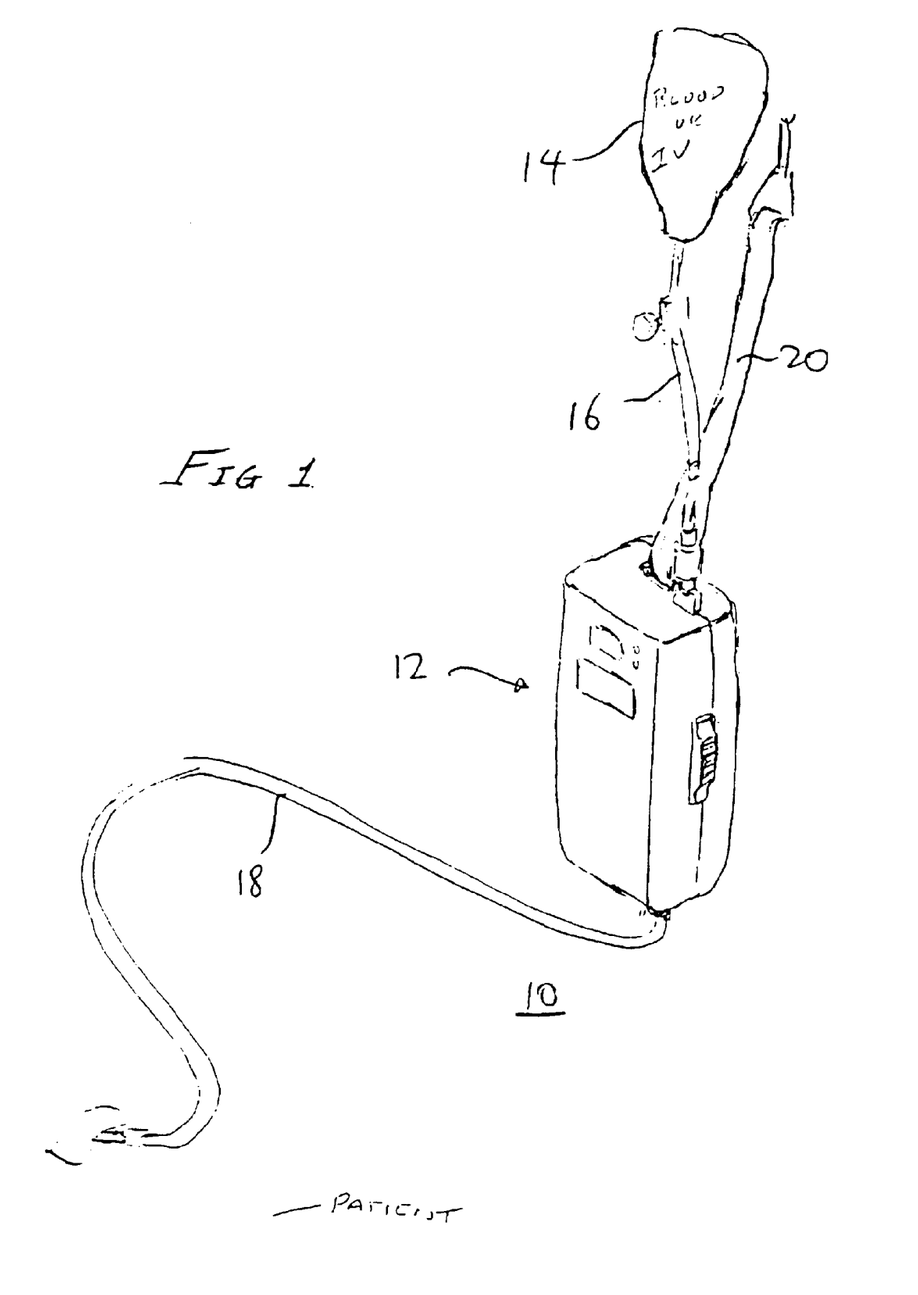
FIG. 1 is a perspective view of a system according to one embodiment of the present invention.
Figure 2:
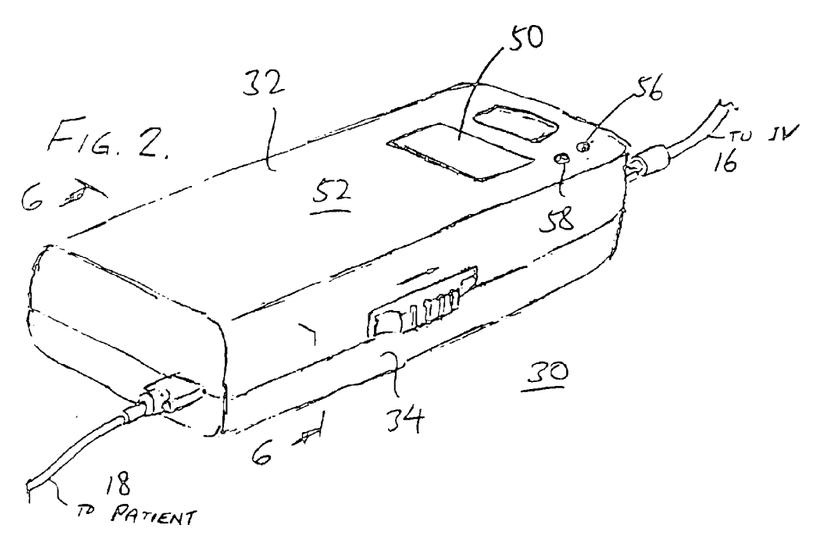
FIG. 2 is a perspective view illustrating one embodiment of a fluid warmer according to the present invention which is shown with the top and bottom shells closed.

FIG. 1 illustrates a heating system 10 according to one embodiment of the present invention. The heating system 10 has a fluid warmer 12 that is coupled to a suspended fluid bag 14 via a first tubing 16. The fluid bag 14 can be a blood bag or an IV solution bag. The first tubing 16 delivers the fluid from the fluid bag 14, and the fluid is warmed by the fluid warmer 12 before being delivered by a second tubing 18 to the patient. A hanging band 20 is formed on an upper portion of the housing of the fluid warmer 12. An annular hanging fixture (not shown) can be attached to a top end of the band 20 for securing the fluid warmer 12 to an IV or other stand. The length of the band 20 can be adjusted by a conventional length adjusting member (not shown) so that the fluid warmer 12 can be hung from the IV stand at an optimal position with respect to the infusion site at the patient.

Alternatively, the band 20 can be replaced by a rigid clamp (not shown) having one end that couples a loop of the fluid warmer 12 and another end that is secured to the stand. This rigid clamp can provide a more stable positioning for the fluid warmer 12 on the stand, since the band 20 can tend to have a swinging effect from time to time.

Figure 3:
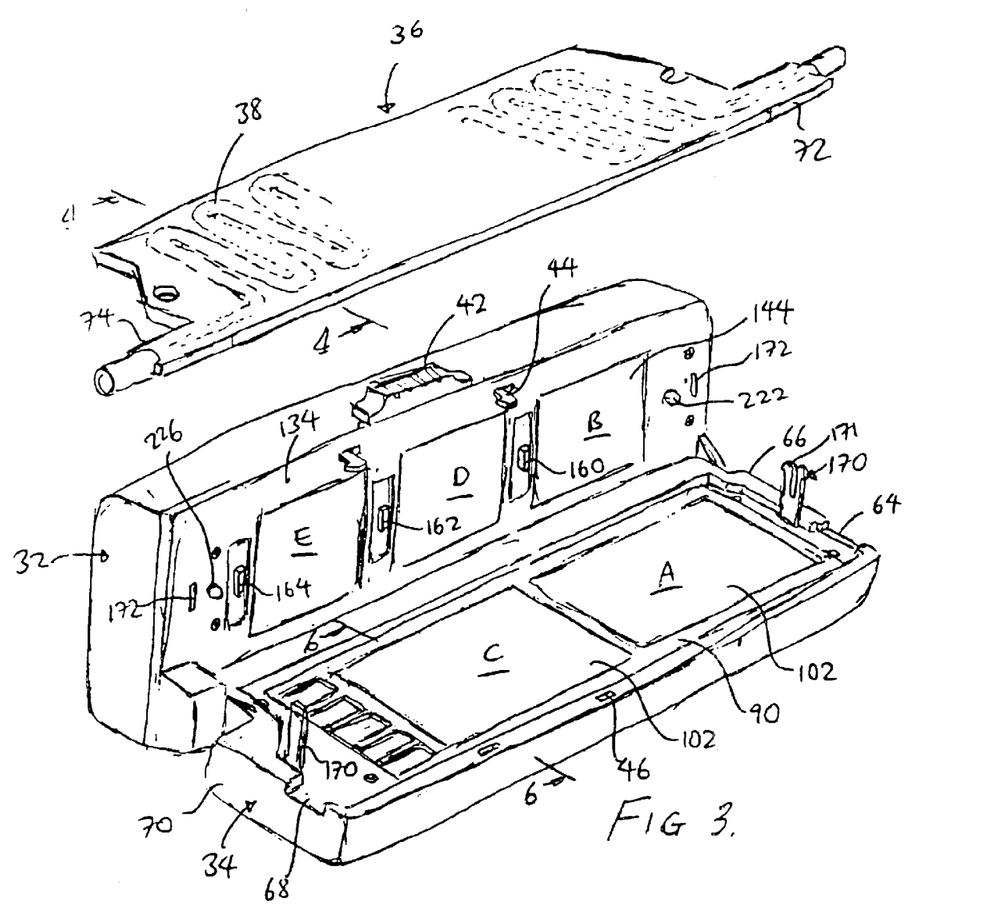
FIG. 3 is an exploded perspective view of the fluid warmer of FIG. 2 showing a disposable cartridge in use therewith.

The fluid warmer 12 according to one embodiment of the present invention is illustrated in greater detail in FIGS. 2, 3, 6A, 6B and 7. The fluid warmer 12 has a case 30 that includes a top shell 32 and a bottom shell 34. A disposable cartridge 36 that is described in greater detail in FIGS. 3–5 below is adapted to be retained between the top shell 32 and the bottom shell 34. The fluid is passed from the first tubing 16 through the channels 38 in the cartridge 36 where the fluid is warmed, and then the warmed fluid is delivered out of the channels 38 to the second tubing 18. The top shell 32 and the bottom shell 34 are made of a synthetic material, and are integrally connected to each other along one side thereof by a hinged connection 40 (see FIG. 6A) so that the top shell 32 can be pivoted with respect to the bottom shell 34 about this hinged connection. As shown in FIG. 3, a sliding lock closure 42 and a hook 44 are provided on the top shell 32 for removably engaging corresponding slots 46 on the bottom shell 34 for securing the top shell 32 to the bottom shell 34.

Figure 6A:
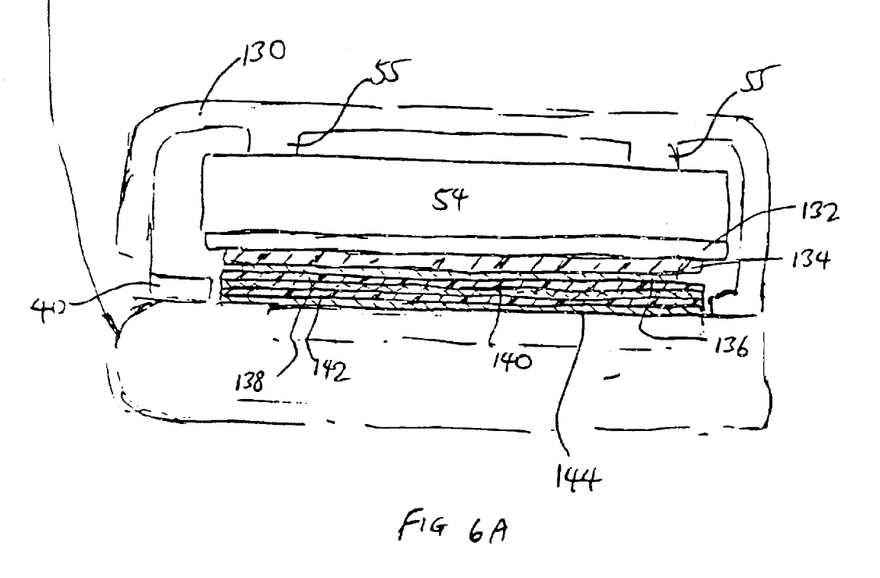
FIG. 6A is a cross-sectional side plan view of the fluid warmer of FIG. 2 taken along line 6—6 thereof.

A display 50 is provided on the back or bottom surface 52 of the top shell 32, and is coupled to a circuit board 54 that is retained inside the top shell 32. The circuit board 54 can be secured inside the top shell 32 by screws through a plurality of threaded posts 55. The circuit board 54 would typically include a processor, a power supply, and other electrical elements that are well-known in the art for controlling and powering a fluid warmer. A green flashing light 56 is provided on the bottom surface 52 and functions to indicate that the warmer 12 is functioning normally. A red light 58 is also provided on the bottom surface 52. When the red light 58 is constantly on, this indicates that the warmer 12 is on. When the red light 58 is flashing, this indicates that the programmed time of 100 hours of use is ending within the next 60 minutes. When this occurs, the warmer 12 must be returned to the factory to be reconditioned and reprogrammed for another 100 hours of use. Of course, those skilled in the art can adapt their own criteria for alerting the users as the usage of the warmer, e.g. use of 500 times by having 500 on and off switching, in order to ensure optimal performance of the warmer.

As shown in FIG. 3, an inlet groove 64 having a U-shaped cross-section is formed along the upper side wall 66 of the bottom shell 34, and an outlet groove 68 having a similar U-shaped cross-section is formed on the opposing side wall 70 of the bottom shell 34. The cartridge 36 is adapted to be fitted into the opened face of the bottom shell 34 with its inlet shoulder 72 fitted into the inlet groove 64 and its outlet shoulder 74 fitted into the outlet groove 68.

Figure 6B:
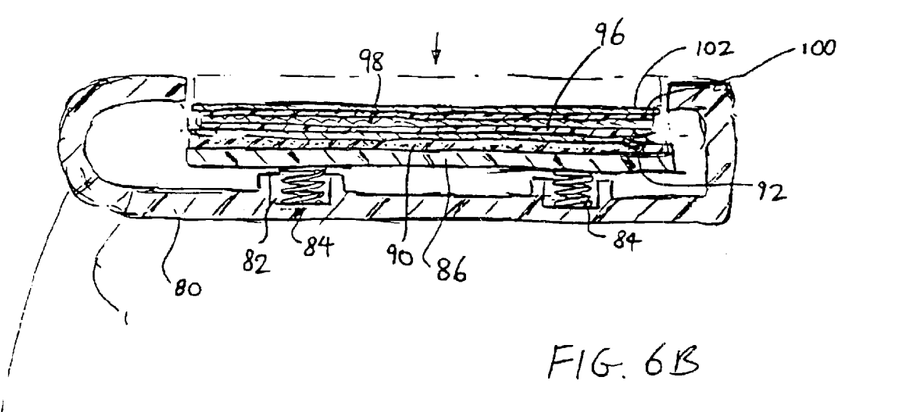
FIG. 6B is a cross-sectional side plan view of the bottom shell of the fluid warmer of FIG. 6A.
Figure 7:
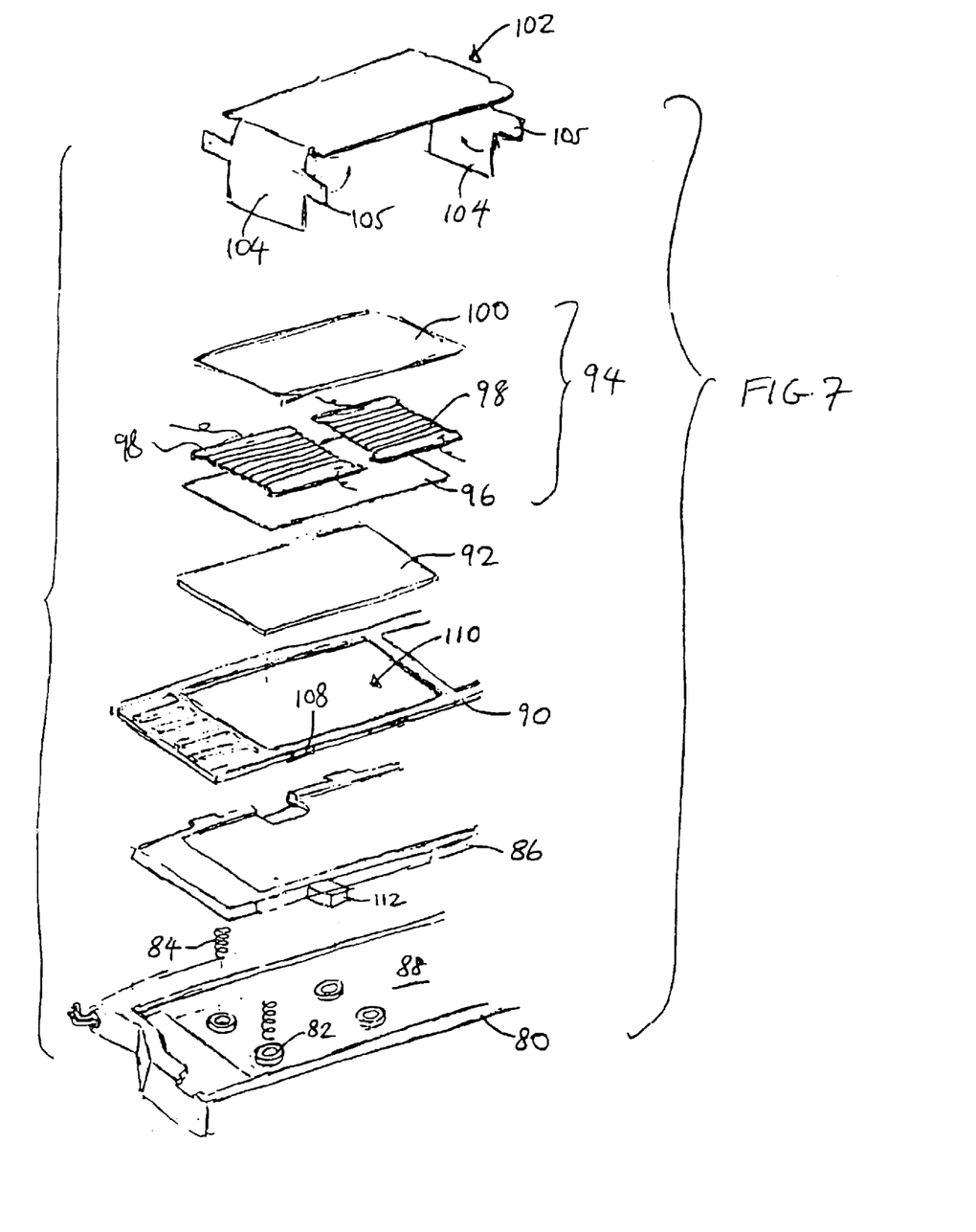
FIG. 7 is an exploded perspective view of the bottom shell of FIG. 6B.

FIGS. 6B and 7 illustrate the various components that are positioned inside the bottom shell 34. The bottom shell 34 has a heating element 94 that is wrapped or enclosed by a heat contact plate 102. The heating element 94 has one or more heating pads 98 that are made up of mica elements that are wound with heat filaments. The heating pads 98 are sandwiched by two conductor pieces 96 and 100. The conductor pieces 96, 100 can also be made of mica or other ceramics. Mica and ceramics are especially well-suited for use in this application since these materials can spread heat evenly without creating hot spots. The heating pads 98 and conductor pieces 96, 100 can be made of the same material, and a non-limiting example of such a material is the "Ceramic Fiber Blanket" marketed by Nichiasu Co., Ltd. of Tokyo, Japan. The heat insulator 92 can be made from a material such as the "Fine Flex" 1300 Paper, Tombo #5130, which is also marketed by Nichiasu Co., Ltd. of Tokyo, Japan. The heating pads 98 and the conductor pieces 96, 100 are then wrapped or enclosed by the heat contact plate 102. The heat contact plate 102 is preferably made of a conducting metal, such as aluminum, and has two opposing legs 104. The heating pads 98 and the conductor pieces 96, 100 are placed under the heat contact plate 102, and the legs 104 are then folded over the bottom of the heating pads 98 and the conductor pieces 96, 100 to enclose or wrap them.

The bottom shell 34 also includes a heat insulator 92 that is positioned under the folded legs 104 of the heat contact plate 102. Ear pieces 105 provided on opposing edges of each leg 104 can be folded so that they extend in a generally horizontal plane (i.e., parallel to the contact plate 102). The combined heating element 94, insulator 92 and heat contact plate 102 are then placed on top of a back plate 86, which is made of a polycarbonate material. A frame 90 is then positioned over the back plate 86, with the ear pieces 105 fitted into openings 108 on the side of the frame 90, so that the combined heating element 94, insulator 92 and heat contact plate 102 are securely retained inside the frame 90 when the frame 90 is heat-sealed to the back plate 86. The frame 90 has large openings or apertures 110 that expose large portions of the heat contact plate 102.

The bottom shell 34 also has a housing 80 having two pieces that are screwed together to hold all the elements (i.e., 102, 94, 92, 90 and 86) of the bottom shell 34 therein. FIG. 7 shows the bottom piece of the housing 80, which has an inner surface 88 that has a plurality of dimples 82, with each dimple 82 retaining a corresponding spring 84. The back plate 86 is seated on top of the springs 84, and has tabs 112 that maintain the back plate 86 inside the housing 80. Electrical wiring and connections (not shown) are provided to couple the filaments on the heating pads 98 with the circuit board 54.

FIG. 6A illustrates the various components that are positioned inside the top shell 32. The elements in the top shell 32 are similar to those in the bottom shell 34. For example, the heating element can be the same as the heating element 94 described above, and can include one or more heating pads 140 that are also configured as filaments wound around mica pieces. The heating pad(s) 140 are sandwiched between heat conductors 138 and 142, which are in turn wrapped or enclosed by a heat contact plate 144. An insulator 136 is positioned under the folded legs of the heat contact plate 144. The combined heating element, insulator 136 and heat contact plate 144 are then placed on top of a back plate 132, which is made of a polycarbonate material. A frame 134 is then positioned over the back plate 132. The frame 134 has large openings or apertures that expose large portions of the heat contact plate 144. The back plate 132 is positioned adjacent the circuit board 54. Electrical wiring and connections (not shown) are provided to couple the filaments on the heating pads 140 with the circuit board 54.

When the fluid warmer 12 is used to warm fluids passing through the cartridge 36, the heating pads 98 and 140 are actuated, and the heat is generated at the filaments and passes through the heat conductors 100 and 142, respectively, and the heat contact plates 102 and 144, respectively, to be transferred to the cartridge 36.

Referring to FIG. 3, temperature control (or overheat) thermistors 160, 162, 164 are attached to spaced-apart locations of the contact plate 144 in a manner such that they slightly project from the contact plate 144. In this embodiment, three thermistors 160, 162 and 164 are arranged to control the warming so that the temperature of the fluid will vary at different regions of the cartridge 36 adjacent the thermistors 160, 162, 164. For example, a first thermistor 160 is positioned adjacent the inlet groove 64 to control the regions A and B of the contact plates 102 and 144, respectively, to a temperature in the range of 32.4 to 39 degrees Celsius. A second thermistor 162 is positioned at about the middle of the top shell 32 to control the regions C and D of the contact plates 102 and 144, respectively, to a temperature in the range of 37.4 to 39 degrees Celsius. A third thermistor 164 is positioned adjacent the outlet groove 68 to control the region E of the contact plate 144 to a desired temperature of 39 degrees Celsius.

In addition, two extensions 170 extend from the frame 90 of the bottom shell 34, and are adapted to be received inside corresponding bores 172 provided in the frame 134 of the top shell 32 to function to align the top and bottom shells 32, 34 when they are closed together. In addition, the two extensions 170 also function to prevent the shells 32 and 34 from opening too far apart so as to prevent the user from touching the heated contact plates 102 and 144. One of the extensions 170 has two prongs 171, each prong 171 having a hooked end that is adapted to lock the bore 172 of the top shell 32. The other extension 170 does not have any prongs, and is generally straight to function to align the closure of the shells 32, 34.

The disposable cartridge 36 is illustrated in FIGS. 3, 4A, 4B and 5. The cartridge 36 is comprised of a central plate 200, a top sheet 202 and a bottom sheet 204. Each of the top and bottom sheets 202, 204 are each made of a film-like and polycarbonate material that effectively conducts heat, and preferably has a thickness of less than 0.03 mm. The thickness of the sheet 202, 204 should be such that it is not too thin (or else the heat will burn the sheet) and not too thick (or else there will be insufficient heat transfer), and it is believed that 0.03 mm is an optimum thickness that meet these objectives. The material is preferably latex-free and does not contain any DEHP (a common plasticizer, Di(2-ethylhexyl) phthalate), because DEHP can leak into the fluid if the added medicine is considered corrosive, thus posing severe health hazard. A non-limiting example of this material is the lupilon Sheet, grade FE2000, that is marketed by Mitsubishi Engineering Plastics Corp., of Tokyo, Japan. The sheets 202 and 204 are laminated or otherwise attached to the two opposing faces or surfaces 206 and 208, respectively, of the plate 200. Alternatively, a single piece of film can be folded and wrapped about the plate 200 to form the two sheets 202, 204. The top and bottom sheets 202, 204 are preferably sized and configured so that they form a unitary piece together with the plate 200 after attachment thereto.

Figure 4A:
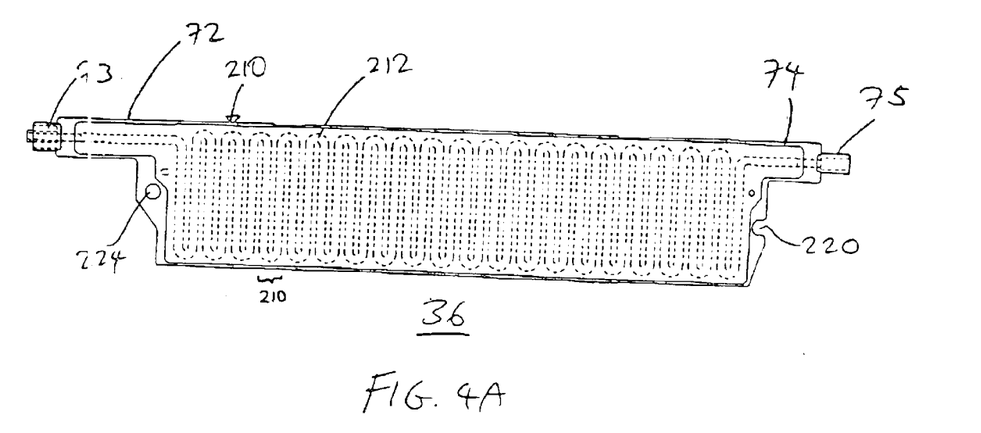
FIG. 4A is a top plan view of the cartridge of FIG. 3.
Figures 4B, 5:
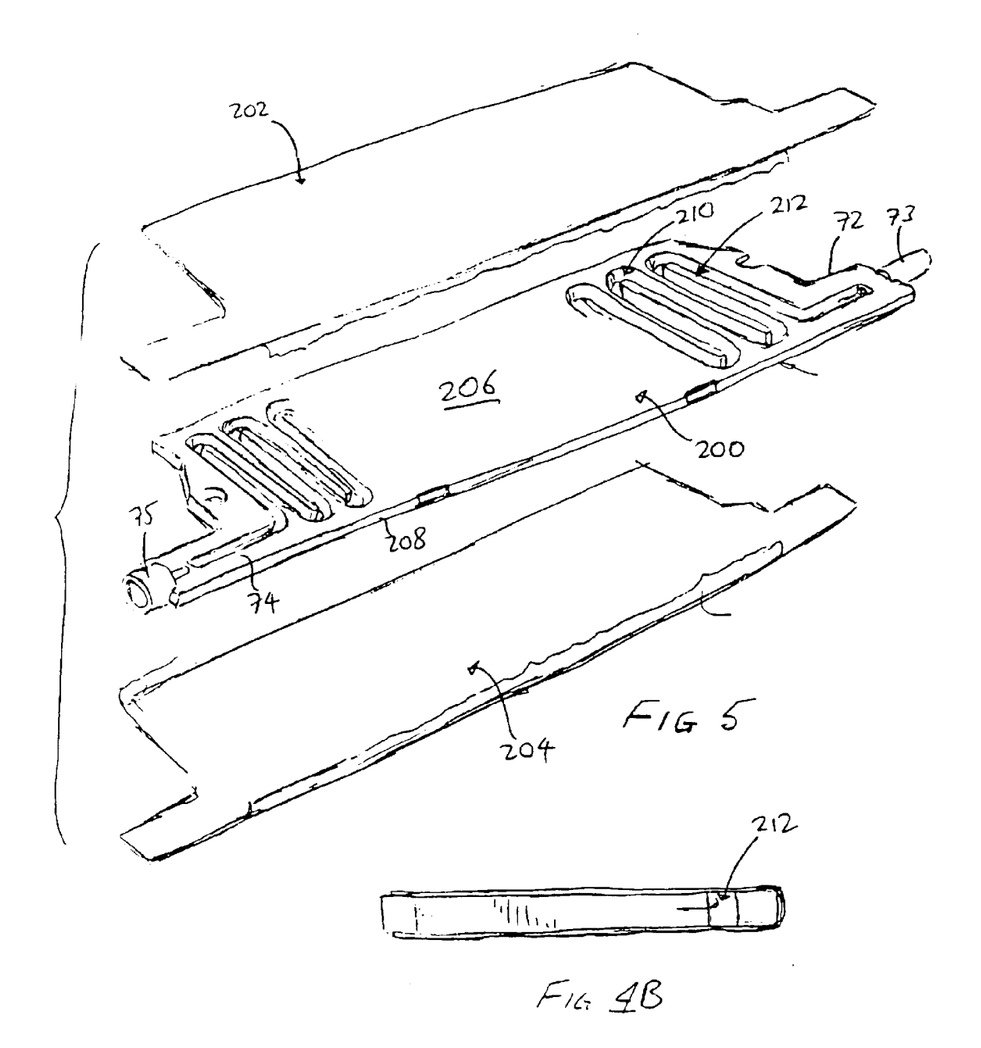
FIG. 4B is a cross-sectional side plan view of the cartridge of FIG. 3 taken along line 4—4 thereof.
FIG. 5 is an exploded perspective view of the cartridge of FIG. 3.

The central plate 200 is made of a rigid material that effectively conducts heat. The plate 200 can also be made of a polycarbonate material that is preferably latex-free and non-DEHP. A non-limiting example of this material is lupilon, grade RF3001 R, that is marketed by Mitsubishi Engineering Plastics Corp., of Tokyo, Japan. The plate 200 can be extruded from a plastic or similar material.

It is important for the materials used for the plate 200 and the sheets 202, 204, or for any container used for medical warming (including without limitation bags, cassettes, or cartridges), to be non-DEHP. Many drugs that are often carried by plastic fluid bags can be quite corrosive and can interact with the DEHP plasticizer (if DEHP is used for the material) to contaminate the fluid being transferred. However, because of the relatively high cost in converting to non-DEHP material, the medical industry has not embraced the idea of using non-DEHP plastic material in all their applications. This is especially the case for fluid or medicine warming.

The plate 200 has an inlet shoulder 72 at one end thereof with an inlet port 73 that leads into a path 212. The path 212 is longitudinal and straight at the inlet shoulder 72, and then meanders in an up and down fashion throughout the body of the plate 200 to form essentially a plurality of alternating U-shaped paths (e.g., one U-shaped path is illustrated at 210). Each U-shaped path 210 reverses its direction of flow at its trough or bottom. The path 212 continues its meandering path of U-shaped paths until it reaches a straight portion at the outlet shoulder 74 that communicates with the outlet port 75. The path 212 is essentially formed by cutting a meandering up-down, alternating and U-shaped path from the body of the plate 200. By attaching the sheets 202, 204 to both surfaces 206, 208 of the plate 200, an actual fluid channel is formed with the sheets 202, 204 acting as side walls to the path 212. The curvature of the U-shapes 210 in the path 212 are measured and configured so that the fluid will not coagulate when the fluid makes the U-shaped turns.

A notch 220 is provided adjacent the inlet side of the cartridge 36 and is adapted to receive a pin 222 that extends from the frame 134. Similarly, a hole 224 is provided adjacent the outlet side of the cartridge 36 and is adapted to receive another pin 226 that extends from the frame 134. These engagements by the pins 222 and 226 in the notch 220 and hole 224 function as alignment and locking mechanisms to secure the cartridge 36 in the desired position between the top shell 32 and the bottom shell 34.

In use, the top shell 32 is opened by pivoting it away from the bottom shell 34. The cartridge 36 can then be placed on the contact plate 102 and the frame 90 of the bottom shell 34. The pins 222 and 226 are aligned with the notch 220 and the hole 224, respectively, to secure the cartridge 36 at the desired position in the bottom shell 34. The top shell 32 can then be pivoted towards the bottom shell 34 to close the warmer 12. The operator (e.g., nurse) can then connect the tubings 16 and 18 in the manner shown in FIG. 1, suspend the warmer 12 from the band 20, and prime the cartridge 36. Fluid from the fluid bag 14 can now flow via the tubing 16 into the cartridge 36, travel through the meandering path 212, and exit the cartridge 36 for delivery to the patient via the tubing 18. The meandering path 212 provides a very long passageway that the fluid must travel through. By requiring the fluid to travel through a long passageway in the cartridge 36, the fluid is essentially required to spend an extended period of time inside the cartridge 36. This extended period of time will allow for sufficient warming of the fluid. This is how the present invention controls the fluid flow rate to allow for consistent and proper warming of the fluid as the fluid travels through the cartridge 36. In addition, the contact area between the sheets 202 and 204 in the cartridge 36 and the heat from the contact plates 102, 144 is increased because there is a greater flat and even surface area on the cartridge 36 to contact the plates 102, 144, thereby promoting more efficient heat transfer.

The construction of the cartridge 36 provides many important benefits. First, the rigid plate 200 has a defined shape and together with its rigidity can therefore maintain integrity under all usage situations. Second, since the shape of the cartridge 26 does not change, the cartridge 36 can be placed inside the warmer 12 after the cartridge 36 has been primed (i.e., filled with fluid). This makes the cartridge 36 portable in nature because patients can be moved around from room to room with the cartridge 36 only, and without the need for the warmer 12 to accompany the cartridge 36. The cartridge 36 can then be used with any other warmer 12 that is located in different rooms. Third, when a nurse squeezes the fluid bag 14 to speed up the flow rate, the cartridge 36 maintains its rigid shape and stays secure inside the warmer 12 because of the locking mechanisms (i.e., the pins 222 and 226, the notch 220 and the hole 224). Fourth, the ports 73 and 75 of the cartridge 36 can be used with standard male/female luer locks, so that hospitals can use generic tubing from the fluid bag 14 to connect to the cartridge 36. Fifth, the cartridge 36 requires a smaller priming volume so that less time is needed to prime the cartridge 36. The low priming volume also contributes to the absence of expansion forces on the sheets 202, 204. Sixth, the rigid structure of the cartridge 36 allows the cartridge 36 to be primed first (outside of the warmer 12), with the nurse observing for any air bubbles. If no air bubbles are visible, then the cartridge 36 can be inserted into the warmer 12 and used with a patient. This improves the safety of the fluid transfer to the patient. Seventh, the rigid structure of the cartridge 36 maintains a constant pressure on the sheets 202, 204 when the cartridge 36 is primed.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A system for warming a fluid, comprising:
    a fluid warmer having a housing that retains therein a heating element,
    said housing comprising an upper section and a lower section hingedly joined at one side of the upper and lower sections, said upper and lower sections adapted to rotatably open; and
    a cartridge that is retained inside the housing and which receives heat from the heating element, comprising:
        a rigid heat-conducting plate having a first surface and a second opposing surface, the plate having a meandering path provided therein; and
        a sheet of heat-conducting film that covers the first and second surfaces, said film being adapted to receive heat from the heating element wherein the fluid warmer includes:
        a heating element;
        a contact plate which thermally couples the heating element with the film of the cartridge, wherein the contact plate has a plurality of separate regions; and
        a plurality of thermistors that are operatively coupled to the cartridge and which are also coupled to a processor, with each of the plurality of thermistors and the processor controlling the fluid traveling through the plurality of separate regions to a different temperature.

2. A system for warming a fluid, comprising:
    a fluid warmer having a housing that retains therein a heating element,
    said housing comprising an upper section and a lower section hingedly joined at one side of the upper and lower sections, said upper and lower sections adapted to rotatably open; and
    a cartridge that is retained inside the housing and which receives heat from the heating element, comprising:
        a rigid heat-conducting plate having a first surface and a second opposing surface, the plate having a meandering path provided therein; and
        a sheet of heat-conducting film that covers the first and second surfaces, said film being adapted to receive heat from the heating element;
wherein the fluid warmer further comprises temperature control thermistors between each contact plate region on the upper section and in contact with opposing contact plates on the lower section.

* * * * *